United States Patent
Lee et al.

(10) Patent No.: US 6,773,803 B2
(45) Date of Patent: Aug. 10, 2004

(54) FAR-INFRARED EMISSION POWDER WITH ANTIBACTERIAL ACTIVITY AND BIO-WAVE STEEL PLATE COATED WITH RESIN CONTAINING SAME

(75) Inventors: Jae-Young Lee, Pohang-si (KR); Eel-Young Kim, Pohang-si (KR); Jin-Gun Sohn, Pohang-si (KR); Noi-Ha Cho, Pohang-si (KR); Ji-Eun Oh, Pohang-si (KR); Jae-Eok Cho, Pohang-si (KR); Jin-Tae Kim, Pohang-si (KR); Jung-Sik Lee, Pohang-si (KR); Yong-Min Kim, Pohang-si (KR)

(73) Assignees: Posco (KR); Research Institute of Industrial Science & Technology (KR)

( * ) Notice: Subject to any disclaimer, the term of this patent is extended or adjusted under 35 U.S.C. 154(b) by 152 days.

(21) Appl. No.: 10/204,151

(22) PCT Filed: Dec. 19, 2001

(86) PCT No.: PCT/KR01/02211

§ 371 (c)(1),
(2), (4) Date: Aug. 16, 2002

(87) PCT Pub. No.: WO02/49985

PCT Pub. Date: Jun. 27, 2002

(65) Prior Publication Data

US 2003/0118665 A1 Jun. 26, 2003

(30) Foreign Application Priority Data

Dec. 19, 2000 (KR) .......................................... 2000-78772
Dec. 23, 2000 (KR) .......................................... 2000-81056

(51) Int. Cl.[7] .................................................. B32B 5/16
(52) U.S. Cl. ........................ 428/323; 478/325; 478/330; 478/332; 478/457
(58) Field of Search ................................ 428/323, 325, 428/330, 332, 457

(56) References Cited

U.S. PATENT DOCUMENTS

| | | | | | |
|---|---|---|---|---|---|
| 5,137,957 A | * | 8/1992 | Asai et al. | ................... | 524/403 |
| 6,166,097 A | * | 12/2000 | Yonemura et al. | ............ | 521/64 |
| 6,313,064 B1 | * | 11/2001 | Miyafuji et al. | ............ | 502/345 |
| 6,395,955 B1 | * | 5/2002 | Roe et al. | ................... | 604/361 |
| 6,534,176 B2 | * | 3/2003 | Terase et al. | ................ | 428/403 |
| 6,677,044 B2 | * | 1/2004 | Araki et al. | ................ | 428/421 |

FOREIGN PATENT DOCUMENTS

| | | |
|---|---|---|
| JP | 08-098897 A | 4/1996 |
| JP | 08-257493 A | 10/1996 |
| JP | 10-297961 A | 11/1998 |
| JP | 2000-063733 A | 2/2000 |
| JP | 2000-171045 A | 6/2000 |
| KR | 1987-0003168 A | 4/1987 |
| KR | 1989-0013156 A | 9/1989 |
| KR | 1992-0012506 A | 7/1992 |
| KR | 1995-0008584 B1 | 8/1995 |
| KR | 146451 B1 | 5/1998 |
| KR | 1998-39182 A | 8/1998 |
| KR | 1998-67390 A | 10/1998 |
| KR | 214449 B1 | 5/1999 |
| KR | 2000-0038422 A | 7/2000 |
| KR | 2001-47688 A | 6/2001 |

* cited by examiner

Primary Examiner—Leszek B Kiliman
(74) Attorney, Agent, or Firm—Webb Ziesenheim Logsdon Orkin & Hanson, P.C.

(57) ABSTRACT

Disclosed are far-infrared emission powders and resin-coated steel plates with antibacterial activity and far-infrared emission properties. In addition to being 0.9 or higher in emissivity, the far-infrared emission powders are inhibitory against the growth of bacteria, with a pH value of 7.5–10.5 in its saturate aqueous solution. A coating material comprising 5–100 parts by weight of the powder per 100 parts by weight of a resin is coated to a dry thickness of 5–60 μm on an electromagnetic shield steel plate without interruption of the intrinsic electromagnetic shield properties of the steel plate.

42 Claims, 14 Drawing Sheets

ZnO

FAR-INFRARED EMISSION POWDER WITH ANTIBACTERIAL ACTIVITY AND BIO-WAVE STEEL PLATE COATED WITH RESIN CONTAINING SAME

BACKGROUND OF THE INVENTION

1. Field of the Invention

The present invention relates to a far-infrared emission powder with antibacterial activity, which can be applied to steel plates to provide antibacterial activity and far-infrared emission properties therefor. Also, the present invention relates to a steel plate which shields electromagnetic waves at low frequencies and can be used where antibacterial activity and far-infrared radiations are required.

2. Description of the Prior Art

Belonging to infrared radiations, far-infrared radiations have wavelengths of as long as 2.5~20 μm. At higher than 0 K, far infrared radiations are generated from all materials, but extensively emitted especially from certain ceramics, so-called far-infrared emitters. So high in energy efficiency are far-infrared radiations owing to their transportation of energy through radiation that they are utilized in a broad spectrum of applications, as disclosed in Korean Pat. Publication No. 95-8584.

For instance, knowledge of the beneficial effect of far-infrared radiations on the body allows the application of far-infrared emitters to sauna construction, electric appliance, general construction, etc.

Representative of far-infrared emitters are jade and elvan, as disclosed in Korean Pat. Application Nos. 88-1616 and 95-26761. Besides, transition metal oxides are known to be high in far-infrared emissivity (Korean Pat. Publication No. 95-8584). Electromagnetic shield capacity cannot be expected from these far-infrared emitters because they have almost no conductivity and permeability.

There are various methods for introducing far-infrared emitting capacity to steel plates. For example, steel plates are coated with far-infrared emitting ceramic to improve their thermal resistance and energy efficiency as disclosed in Japanese Pat. Laid-Open Publication No. 2000-171045. Stainless steel plates can be made into far-infrared emitters by corrosion, as disclosed in Korean Pat. Application No. 90-22365. Korean Pat. Laid-Open Publication No. 1998-83239 introduces a method for making far-infrared emitting steel plates, in which a thermosetting resin such as a polyethylene resin is added with a zeolite powder containing far-infrared emitting ceramics such as $Al_2O_3$, $SiO_2$, etc., and thermally treated. However, the steel plates show a far-infrared emissivity of only less than 0.90 over the whole wavelength ranges because unsuitable far-infrared emitters are selected. Particularly, their far-infrared emissivity is only on the order of 0.5–0.8 in the wavelength band ranging from 5 to 8 μm, which is known to be beneficial to the health of the body.

Referring to FIGS. 4a and 4b, there are emission curves are displayed. Emissivity of conventional PCM (pre coated metal) steel plate are plotted versus wavelengths in FIG. 4a. FIG. 4b shows typical emission power of PCM steel plate and an ideal body and are plotted versus wavelengths. As seen in the curves, these steel plates do not show high efficiency far-infrared emission. Additionally, these steel plates are not expected to shield electromagnetic waves at low frequencies.

As conditions demand, steel plates are required to be inhibitory against microbes, as well as showing high far-infrared emissivity. In this regard, many prior arts suggest that antibacterial materials are applied to steel plates for use in interior finishes, kitchenware, etc. For example, Korean Patent Application No. 1996-58162 discloses silver (Ag) impregnated in a phosphate material as an antibacterial material applicable to steel plates. Likewise, inorganic materials of antibacterial activity such as Zn and Ag are impregnated in zeolite carriers that are of far-infrared emission, as disclosed in Japanese Pat. Laid-Open Publication No. Hei. 8-257493 and Korean Pat. Laid-Open Publication No. 1998-83239. Another example of the antibacterial materials applicable to steel plates is a photocatalyst such as $TiO_2$ (Japanese Pat. Laid-Open No. 2000-63733). Further, U.S. Pat. No. 6,313,064 utilizes the catalytic activity of metal in combination with $TiO_2$ in allowing for the antibacterial activity of steel plates. Most of the conventional antibacterial materials applied to steel plates are based on the antibacterial activity of metal ion and optical properties of $TiO_2$. However, the carriers containing antibacterial metal ion and photocatalysts are very expensive in addition to being poor in far-infrared emissivity.

Consisting of time-varying electric and magnetic fields which interact differently with biological systems, electromagnetic waves were found to have detrimental effects on the body, which has led to the development of various methods and materials for shielding electromagnetic waves. Artificial waves adversely affecting the body are collectively called harmful waves.

Recent studies have demonstrated harmful effects of electromagnetic waves at low frequencies on biological systems. Particularly, a series of studies which revealed the interrelation of the electromagnetic field (60 Hz) around power transmission lines and carcinogenesis has had great repercussions all over the world.

In addition to carcinogenic effects, low frequency waves with magnetic properties were found to cause inductive currents in the body upon exposure to the waves for a long period of time, upsetting the biological balance of various ions, such as $Na^+$, $K^+$, $Cl^-$ and so forth, across cellular membranes, which adversely affects the hormone secretion and immunocytes of the body. A study has been reported that a magnetic field changes secretion amount of melatonin related with sleep and thus brings insomnia in long-term health effect.

Recent legislation, in response to environmental concerns stemming from adverse health effects of electromagnetic fields, has been enacted to lower the acceptable levels of electromagnetic waves emitted from various electrical or electromagnetic appliances in many countries. Further, the regulation concerning electromagnetic waves is used as an import barrier against electric and/or electromagnetic appliances. For example, Sweden and other European countries prohibit the import of TVs or computer monitors that show a magnetic leakage of 2 mG or higher.

Likewise, with electromagneticity related academic societies (Korea Electromagnetic Engineering Society) and medical societies as central figures, Korean governmental and non-governmental organizations have made much effort to enact a law which regulates exposure limits of electric and magnetic fields (Journal of the Korea Electromagnetic Engineering Society Vol. 8, No. 2, 1997; White Paper on the Activity at National Assembly of the Committee on the Problems of Harmful Electromagnetic Waves, issued December 1999; "Epiodemiological Investigation for the Influence of Electromagnetic Waves on the Body and Study on the Enactment of Law Regulating Electromagnetic Waves", Korea Radio Station Management Agency (KORA 99-09, August 2000).

In order to cope with such harmful electromagnetic waves, shielding technology has been developed in two aspects: construction and material. Copper and aluminum are currently in use as shields against electromagnetic waves. Also, the present inventors described a steel material with excellent magnetic shield effect at low frequencies in Korean Pat. Application No. 1999-52018. However, such non-iron materials and the steel plates with excellent electromagnetic shield capacity are not suitable as far-infrared emitters owing to their poor far-infrared emissivity.

SUMMARY OF THE INVENTION

Leading to the present invention, the intensive and thorough research, conducted by the present inventors, resulted in the finding that certain alkaline oxides have excellent far-infrared emissivity as well as inhibitory activity against microbes, and can be applied to steel plates.

Therefore, it is an object of the present invention to overcome the above problems encountered in the prior art and to provide a far-infrared emission powder which is of antibacterial activity with an alkaline pH in its saturate aqueous solution and shows far-infrared emission activity.

It is another object of the present invention to provide a resin-coated steel plate, which is of antibacterial activity and shows far-infrared emission activity.

It is a third object of the present invention to provide electromagnetic waves shielding steel plate coated resin containing far-infrared emission powder, which has shielding electromagnetic waves as well as antibacterial activity and far-infrared emission property.

In accordance with an aspect of the present invention, there is provided a far-infrared emission powder, which is of antibacterial activity with a pH value ranging from 7.5 to 10.5 in its saturated aqueous solution, and shows a far-infrared emissivity of 0.9 or higher.

In accordance with another aspect of the present invention, there is provided a resin-coated steel plate with antibacterial activity and far-infrared emission properties, having a resinous coating at a dry thickness of 5 to 60 μm, said resinous coating comprising 5–100 parts by weight of a far-infrared emission powder per 100 parts by weight of a resin, said powder having a pH value ranging from 7.5 to 10.5 in its saturate aqueous solution, and showing a far-infrared emissivity of 0.9 or higher.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1A:
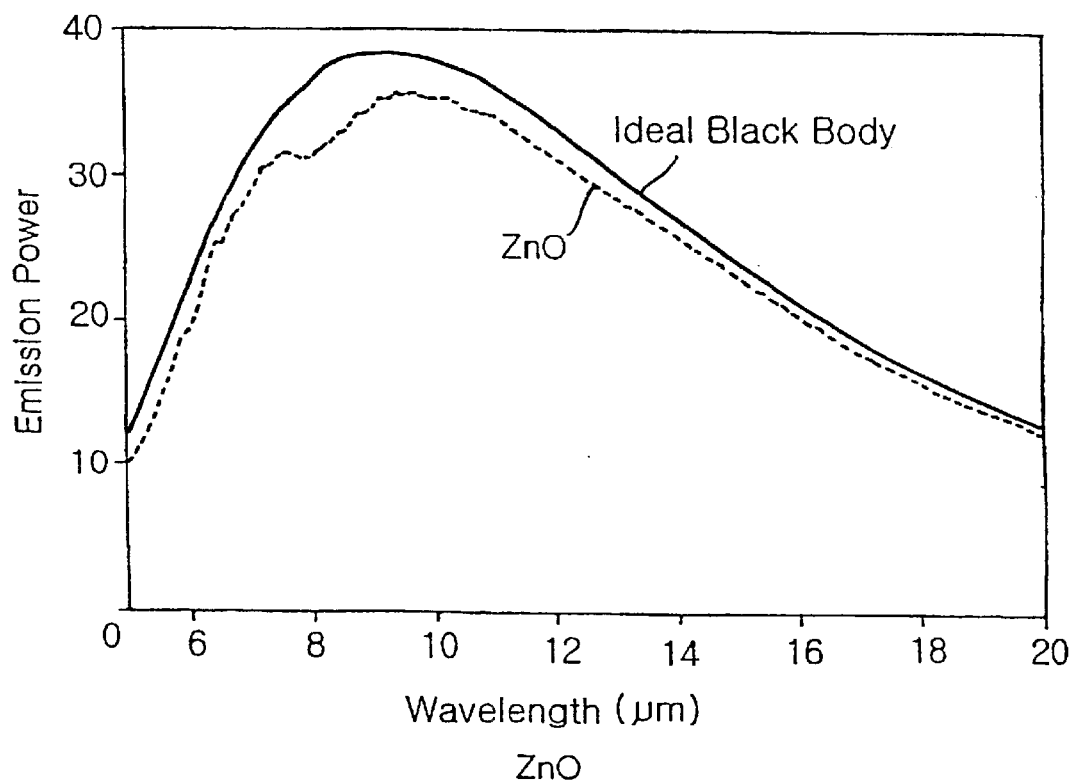
FIG. 1a shows far-infrared emission curves of a ZnO powder and an ideal black body.

When being in contact with moisture, certain alkaline metal oxide powders have hydroxides in the form of M(OH) or $M(OH)_2$ (wherein M is an alkaline metal element) at their surfaces. These hydroxides are of weak alkalinity while showing excellent far-infrared emission and potent antibacterial activity.

Owing to their high solubility in water, $Na_2O$, $K_2O$ and CaO powders readily react with moisture to form NaOH, KOH and $Ca(OH)_2$, respectively, with concurrent production of great heat. In addition, the solution of $Na_2O$, $K_2O$ or CaO in water is highly alkaline with a pH of 11 or higher. Thus, the oxides are not suitable as far-infrared emission powder because of its higher alkalinity, which is harmful to body, even if $Na_2O$, $K_2O$ and CaO in the form of powder exhibit antibacterial activity.

By contrast, MgO and ZnO powders hardly react with moisture or water. When MgO and ZnO powders are brought into direct contact with water or moisture, only a very small quantity of them are formed into hydroxides with which the pH on the surface of the powders then falls within the range of 7.5 to 10.5. At the surface of the alkaline oxide powders, the reaction with moisture is conducted as shown in the following chemical formula 1:

$$MgO, ZnO + 2H_2O \longrightarrow Mg(OH)_2, Zn(OH)_2 \qquad [1]$$

Generally, microbes are vulnerable to environment changes. When the pH of the environment is moved to the range of 7.5 to 10.5, growth of some microbes may be effectively inhibited. The weak alkaline pH range is harmless to the body so that the hydroxides or oxides are utilized in making spa-like water, alkaline foods, antacid, etc.

In contrast to MgO and ZnO, $CaCO_3$ does not show antibacterial activity by changing environmental pH. $CaCO_3$ powder itself is of activity against bacteria, with little solubility in water. However, the antibacterial activity of $CaCO_3$ is weaker than that of MgO or ZnO. Where $CaCO_3$ in combination with resin is coated on steel plates to provide them with antibacterial activity, $CaCO_3$ must be used in a larger amount than MgO, ZnO, $Mg(OH)_2$ and $Zn(OH)_2$. Further, MgO, ZnO, $Mg(OH)_2$, $Zn(OH)_2$, and $CaCO_3$ all show a far-infrared emissivity of 0.90 or higher, preferably 0.92 or higher in the far-infrared band.

Ceramic powder which shows a far-infrared emissivity of 0.90 or higher, preferably 0.92 or higher, and gives a pH of 7.5 to 10.5 or has antibacterial activity naturally can be used as antibacterial, far-infrared emission powder (hereinafter referred to just as "emission powder") in accordance with the present invention.

Examples of the emission powder, just illustrative, but not limitative, include powder of MgO, $Mg(OH)_2$, ZnO, $Zn(OH)_2$, $CaCO_3$ or mixtures thereof.

In accordance with an embodiment of the present invention, MgO, $Mg(OH)_2$, ZnO, $Zn(OH)_2$, $CaCO_3$ or mixtures thereof, antibacterial and far-infrared emissive, are preferably contained in an amount of 17% by weight or more in an emission powder. If the oxides or hydroxides are used in an amount less than 17% by weight, they(the powders) do not show excellent far-infrared emissivity.

The emission powder preferably has a specific surface area of 1.0 $m^2/g$ or more. Also, preferred is an emission powder with a particle size of 100 meshes or less. When being coated in combination with a binder, a far-infrared emission powder with a small specific surface area or a large particle size causes the coating to be formed non-uniform.

The emission powder of this invention can be prepared any known method. For example, $Mg(OH)_2$ may be obtained by the hydration of alkaline refractory materials from iron and steel manufacturing mill. In detail, when magnesium oxide (MgO), used as an alkaline refractory material for manufacturing steel and iron, is heated and aged in an aqueous solution at 100° C. or higher, magnesium hydroxide is formed on the refractory material. Alternatively, magnesium hydroxide is obtained from seawater.

Since powder containing MgO, $Mg(OH)_2$, ZnO, $Zn(OH)_2$, $CaCO_3$ or mixtures thereof is white in color, it is admixed with colorful pigment with the maintenance of the color or the pigment. Thus, a far-infrared emission to be coated on substrates such as steel plates and plastics, can be obtained with desired color.

In addition to being superior in terms of far-infrared emissivity and antibacterial activity, powder containing MgO, $Mg(OH)_2$, ZnO, $Zn(OH)_2$, $CaCO_3$ or mixtures thereof is harmless to the body. Therefore, the emission powder of the present invention, in combination with paint or resin, can be applied to any place where antibacterial activity and healthful far-infrared emission are required. Illustrative, but not limitative examples of the applications that the emission power of the present invention has, include resin-coated steel plates, wallpaper, furniture, and plastic cases.

For application to steel plates, as mentioned above, the emission powder is combined with a resin. Any resin, which is applied to steel plates can be used to combine with the emission powder of the present invention. Illustrative, non-limiting examples of the resin useful in the present invention include polyester resins and acryl resins.

In accordance with the present invention, the emission powder is used in an amount of 5 to 100 parts by weight, based on 100 parts by weight of a resin and preferably in an amount of 15 to 100 parts by weight. For example, when the emission powder is used in an amount of less than 5 parts by weight, poor antibacterial activity and far-infrared emission properties result. Meanwhile, the far-infrared radiation is greater as the content of the emission powder in a resin is higher. Considering only the far-infrared radiation factor, it is better to use more emission powder. However, more than 100 parts by weight of the emission powder in 100 parts by weight of the resin results in deteriorating coating adhesion and compatibility with other components such as pigment.

However, the emission powder quantity needed for critical antibacterial activity differs from one emission powder to another. For instance, the minimal emission powder quantity required to allow a resin-coated steel plate to have an antibacterial potency of 90% or higher is dependent on the emission powder used. In detail, in order to provide an antibacterial potency of 90% or higher for a steel plate, MgO or $Mg(OH)_2$ must be used in an amount of 5 parts by weight or more based on 100 parts by weight of a resin, ZnO or $Zn(OH)_2$ in an amount of 20 parts by weight or more, and $CaCO_3$ in an amount of 30 parts by weight or more.

As occasions demand, the resin composition for coating steel plates may comprise a curing agent, a dulling agent, a dispersing agent, and other additives, in addition to the emission powder, in accordance with the present invention.

When the resin containing the far-infrared emission powder is coated on a steel plate, the far-infrared emissivity of the steel plate increases to some degree with the thickening of the resulting coating. For example, when the coating composition containing the emission powder is coated to a dry thickness of 5 $\mu$m on a steel plate, the coating has an antibacterial potency of 90% or higher and a far-infrared emissivity of 0.85 or more. At a dry thickness of 15 $\mu$m, the coating exhibits a far-infrared emissivity of 0.90 or more. However, the far-infrared emissivity increases until the dry thickness reaches 60 $\mu$m. A dry thickness greater than 60 $\mu$m may bring about a reduction in coating adhesion rather than increase the far-infrared emissivity. In the case of PCM(pre-coated metal) steel plate, the coating preferably has a dry thickness less than 30 $\mu$m. In consideration of the above conditions, the resin containing the emission powder is preferably coated to a dry thickness of 5 to 60 $\mu$m on steel plates and preferably to a dry thickness of 15 to 30 $\mu$m.

It is preferred that the far-infrared emission powder is contained in an amount of approximately 25 to 50% by weight in the resin coating. For example, if the content of far-infrared emission powder is less than 25% by weight, the emissivity becomes poor. On the other hand, the emissivity is not further increased when more than 50% by weight of the emission powder is used.

Figure 5:
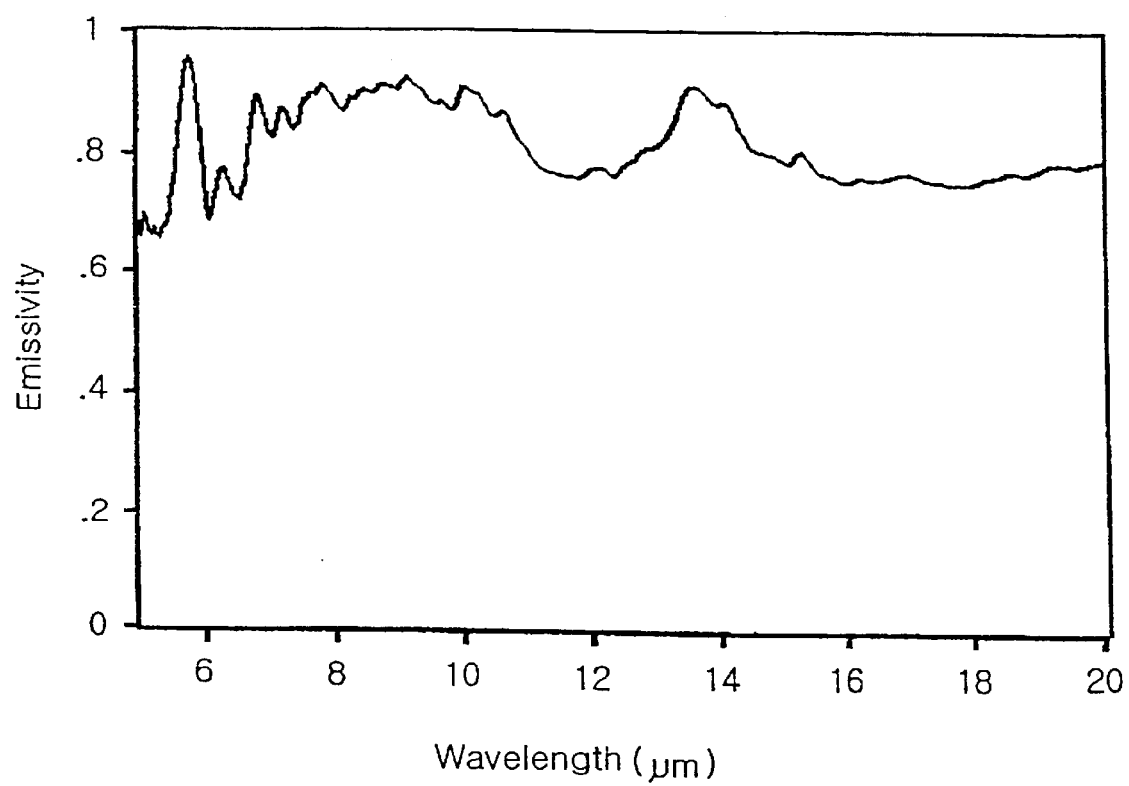
FIG. 5 is a curve in which far-infrared emissivity of a polyester resin is plotted versus wavelengths.
Figure 6A:
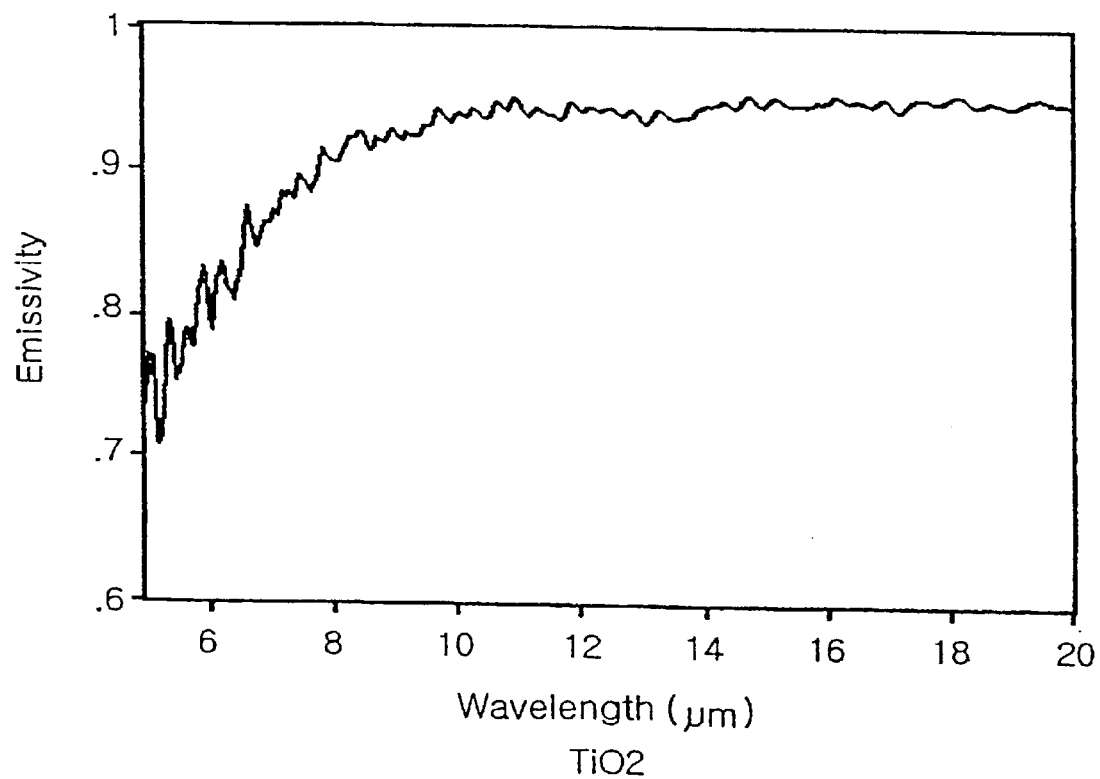
FIG. 6a is a curve in which far-infrared emissivity of a $TiO_2$ powder is plotted versus wavelengths.
Figure 6B:
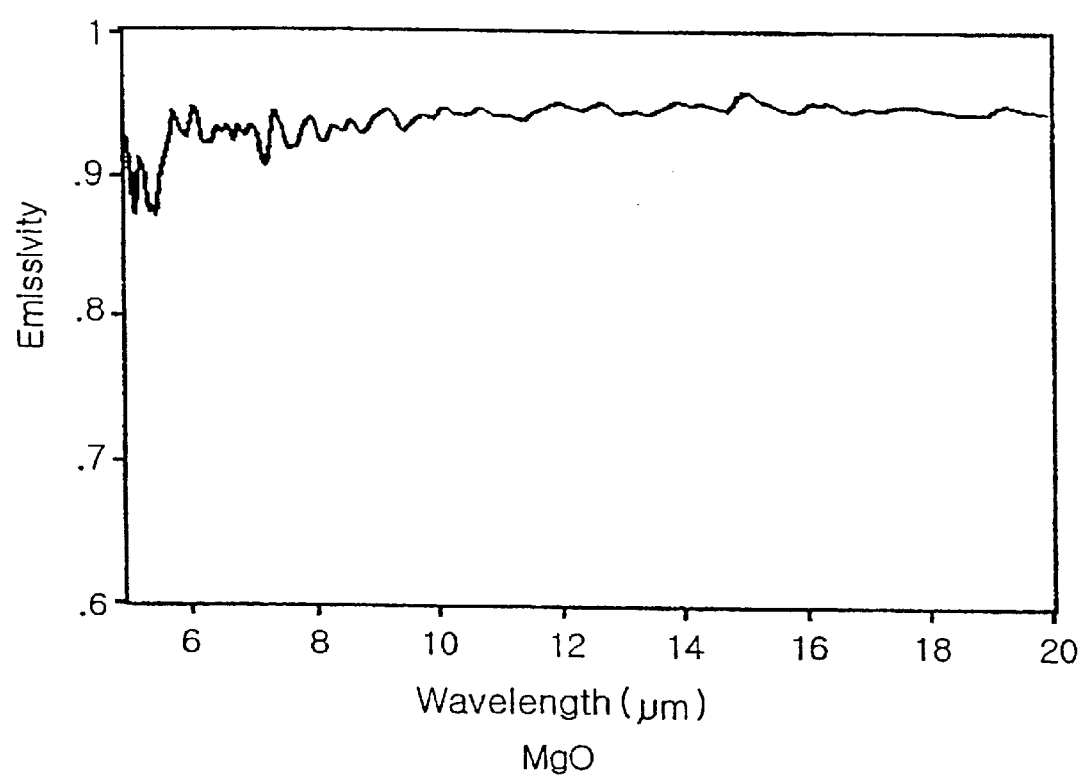
FIG. 6b is a curve in which far-infrared emissivity of a MgO powder is plotted versus wavelengths.
Figure 6C:
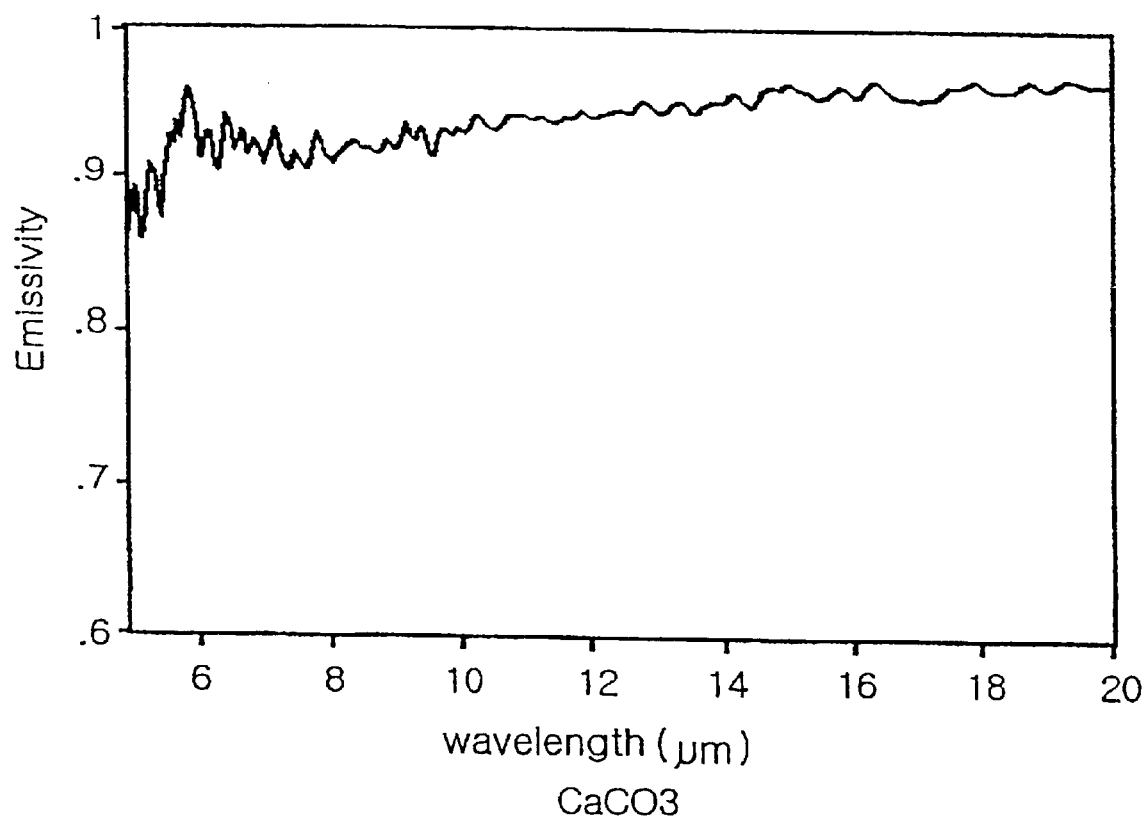
FIG. 6c is a curve in which far-infrared emissivity of a $CaCO_3$ powder is plotted versus wavelengths.
Figure 6D:
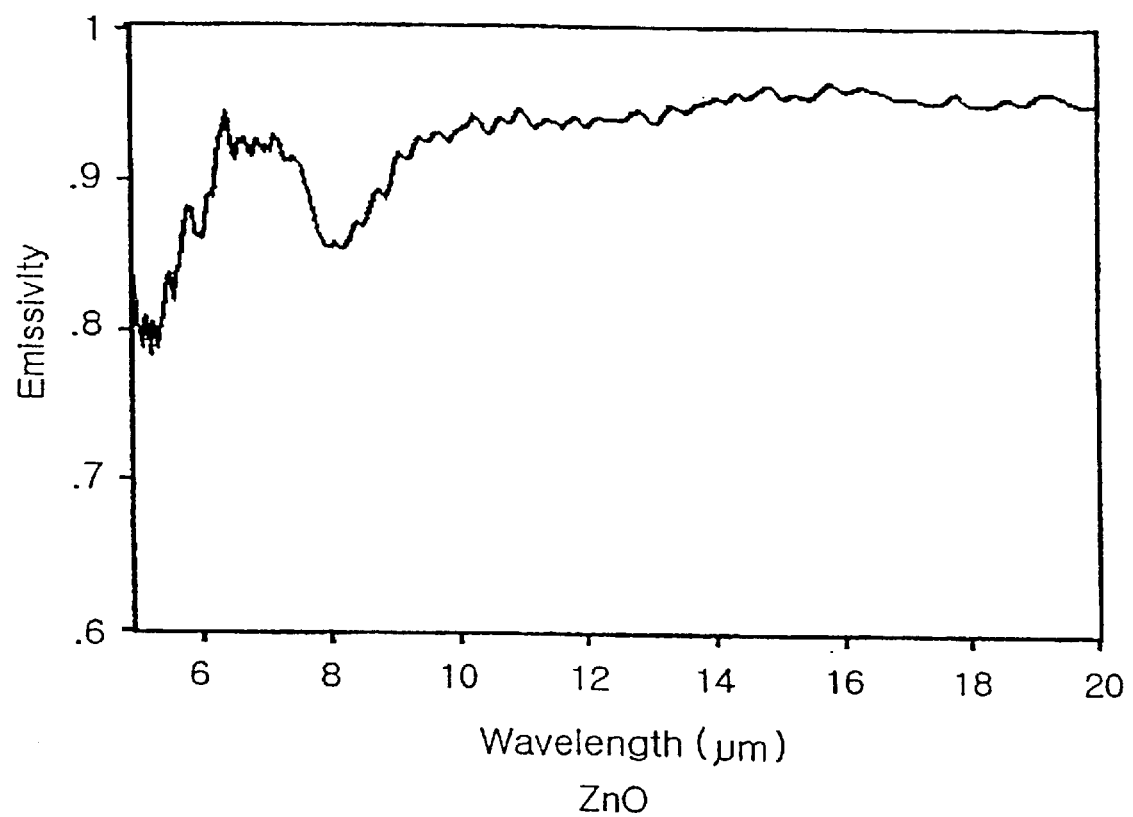
FIG. 6d is a curve in which far-infrared emissivity of a ZnO powder is plotted versus wavelengths.

In the wavelength band of 5 to 8 $\mu$m, which is beneficial to the body, polyester resins have a far-infrared emissivity of 0.5 to 0.8, which is significantly poor compared to the far-infrared emissivity in the other wavelength band out of the range of 5 to 20 $\mu$m, as shown in FIG. 5. When using a polyester resin used, therefore, it is required to use an emission powder which shows high far-infrared emissivity in the wavelength band of 5 to 8 $\mu$m, thereby the polyester resin-coated steel plate is required to have a far-infrared emissivity of 0.85 or higher in the wavelength band of 5 to 8 $\mu$m and a far-infrared emissivity of 0.90 or higher over the other range out of whole far-infrared wavelength band from 5 to 20 $\mu$m.

MgO, $Mg(OH)_2$, ZnO, $Zn(OH)_2$, and $CaCO_3$ all show a far-infrared emissivity of 0.90 or higher in the wavelength band of 5 to 8 $\mu$m. Hence, in the present invention, any one selected from among MgO, $Mg(OH)_2$, ZnO, $Zn(OH)_2$, $CaCO_3$ and mixtures thereof is combined with a polyester resin and applied to a steel plate to accomplish a desired far-infrared emissivity in the wavelength band of 5 to 8 $\mu$m.

On a steel plate, a polyester resin comprising the far-infrared emission powder is coated to a dry thickness of 15 to 60 μm and preferably to a dry thickness of 15 to 30 μm in accordance with the present invention. For example, if the coating thickness is below 15 μm, there is not obtained a sufficient far-infrared emissivity. On the other hand, a coating thicker than 60 μm shows poor coating adhesion to the steel plate.

When being coated with a polyester resin mixed with a far-infrared emission powder which shows a far-infrared emissivity of 0.90 or higher in the wavelength band of 5 to 8 μm, a steel plate is found to have a far-infrared emissivity of 0.90 or higher, on average, in the whole far-infrared wavelength band of 5 to 20 μm and a far-infrared emissivity of 0.85 or higher in the wavelength band of 5 to 8 μm.

It should be understood that the emission powder of the present invention does not limit the steel plates useful in the present invention. Any steel plate may be used if the emission powder in the present invention is applied thereto. Furthermore, a resin mixed with the far-infrared emission powder of the present invention is coated on an electromagnetic shield steel plate, thereby producing a bio-wave steel plate which is superior in terms of antibacterial activity and far-infrared emission, as well as exhibiting excellent electromagnetic shield effect. The term "bio-wave steel plate" as used herein means a steel plate which shields harmful electromagnetic waves (e.g., artificially made electromagnetic fields at 60 Hz) and emits healthful far-infrared radiations.

The electromagnetic shield steel plate useful in the present invention is exemplified by a steel plate which has a maximum permeability of 2,000 or higher under a time-varying magnetic field at 60 Hz, but is not limited thereby.

A steel plate which comprises iron in an amount of 95% by weight or higher with carbon in an amount of 0.02% by weight or less, can show a maximum permeability of 2,000 or higher under a time-varying magnetic field at 60 Hz.

A carbon content more than 0.02% by weight lowers the maximum permeability under a time-varying magnetic field (60 Hz), leading to a reduction in electromagnetic shield effect. Useful in the present invention are cool-rolled steel plates comprising C in an amount of 0.02% by weight or less and Fe in an amount of 95% by weight or higher and silicon steel plates comprising Si in an amount of 0.5 to 3.5% by weight. These steel plates may be galvanized with zinc in an electrolytic or hot-dip manner, chromated, or coated with a resin.

The antibacterial emission powder and bio-wave steel sheet can be used to control or remove fungi, particularly *E. coli* and *Pseudomonas aeruginosa*. Thus, the bio-wave steel plate of the present invention may be used where not only electromagnetic shield and far-infrared emission but also the removal of *E. coli* and *Pseudomonas aeruginosa* is required.

Having generally described this invention, a further understanding can be obtained by reference to certain specific examples which are provided herein for purposes of illustration only and are not intended to be limiting unless otherwise specified.

EXAMPLE 1

To 100 g of water was added 30 g of each of the alkaline oxides and hydroxides shown in the following Table 1. After the addition of the alkaline oxides or hydroxides, the aqueous solutions were measured for pH and the results are given in Table 1. The distilled water prior to the addition of the alkaline oxides or hydroxides was measured to be pH 6.7.

Figure 1B:
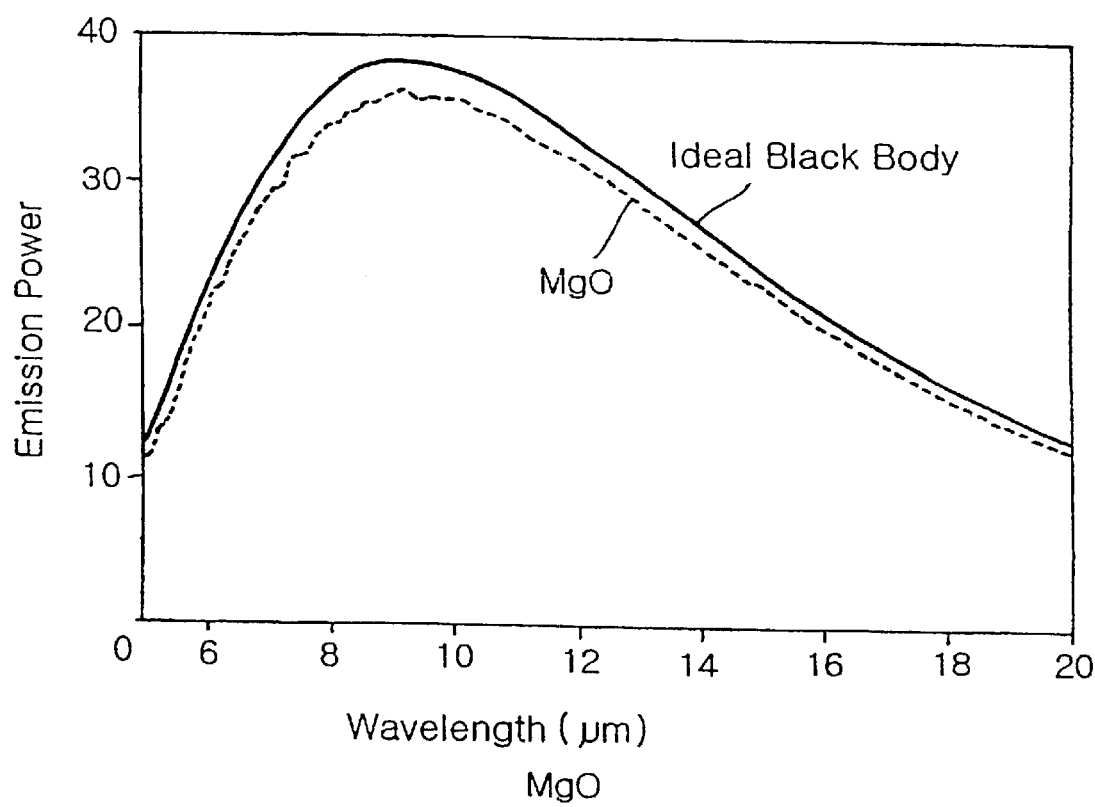
FIG. 1b shows far-infrared emission curves of a MgO powder and an ideal black body.
Figure 2A:
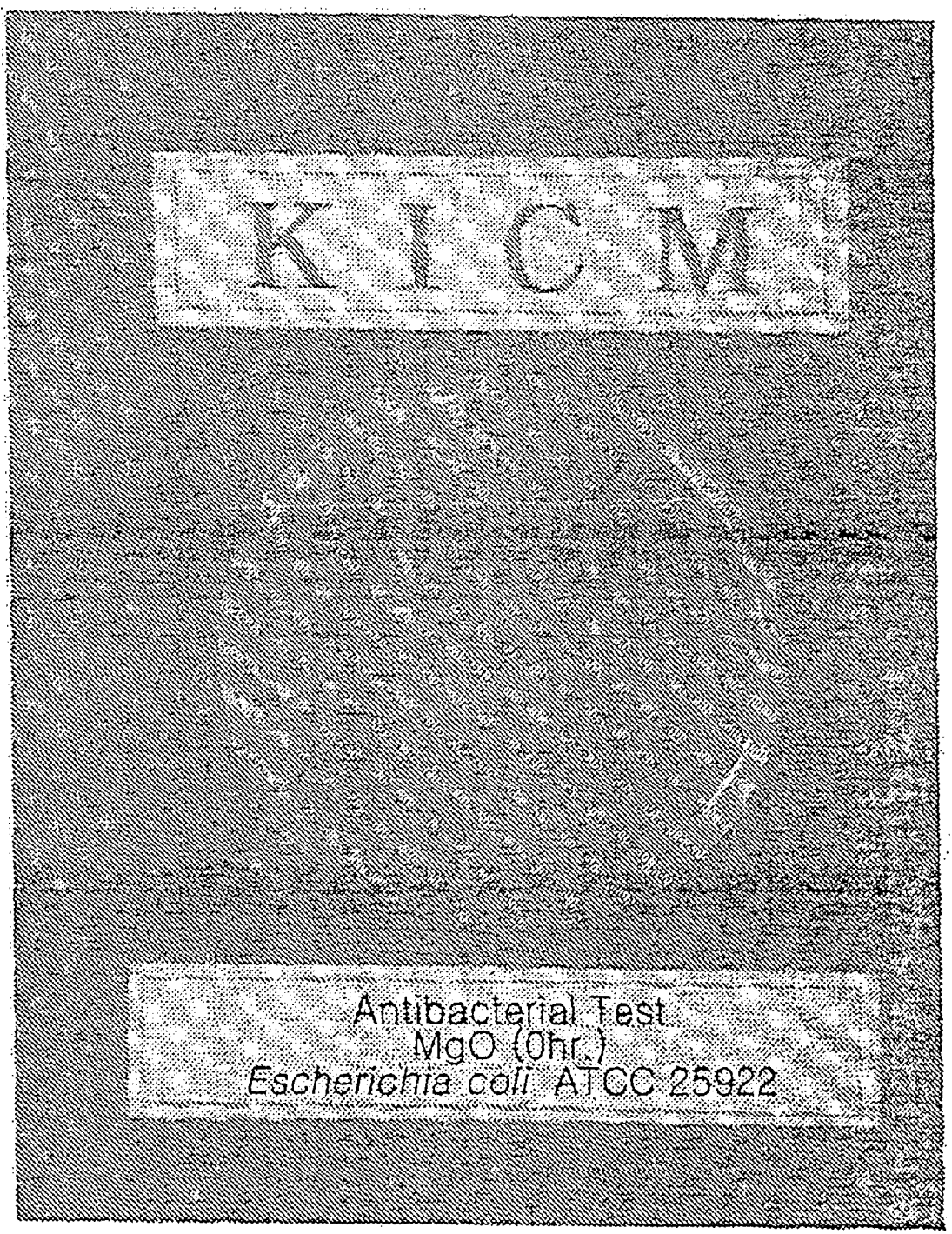
FIG. 2a is a photograph showing a standard sample comprising MgO combined with magnesium hydroxide, and *E. coli;*
Figure 2B:
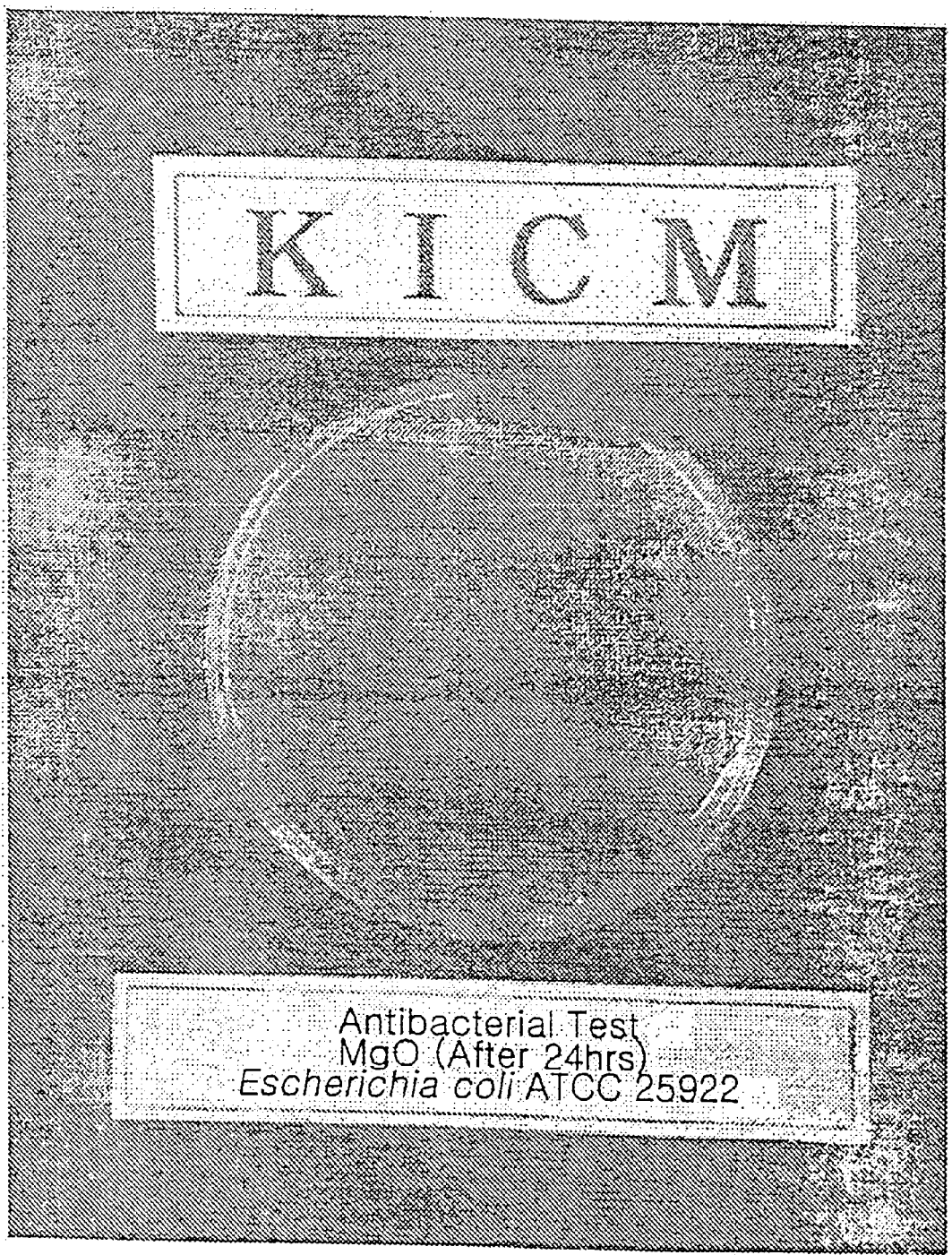
FIG. 2b is a photograph showing the growth of *E. coli* after culturing the standard sample of FIG. 2a for 24 hours.
Figure 3A:
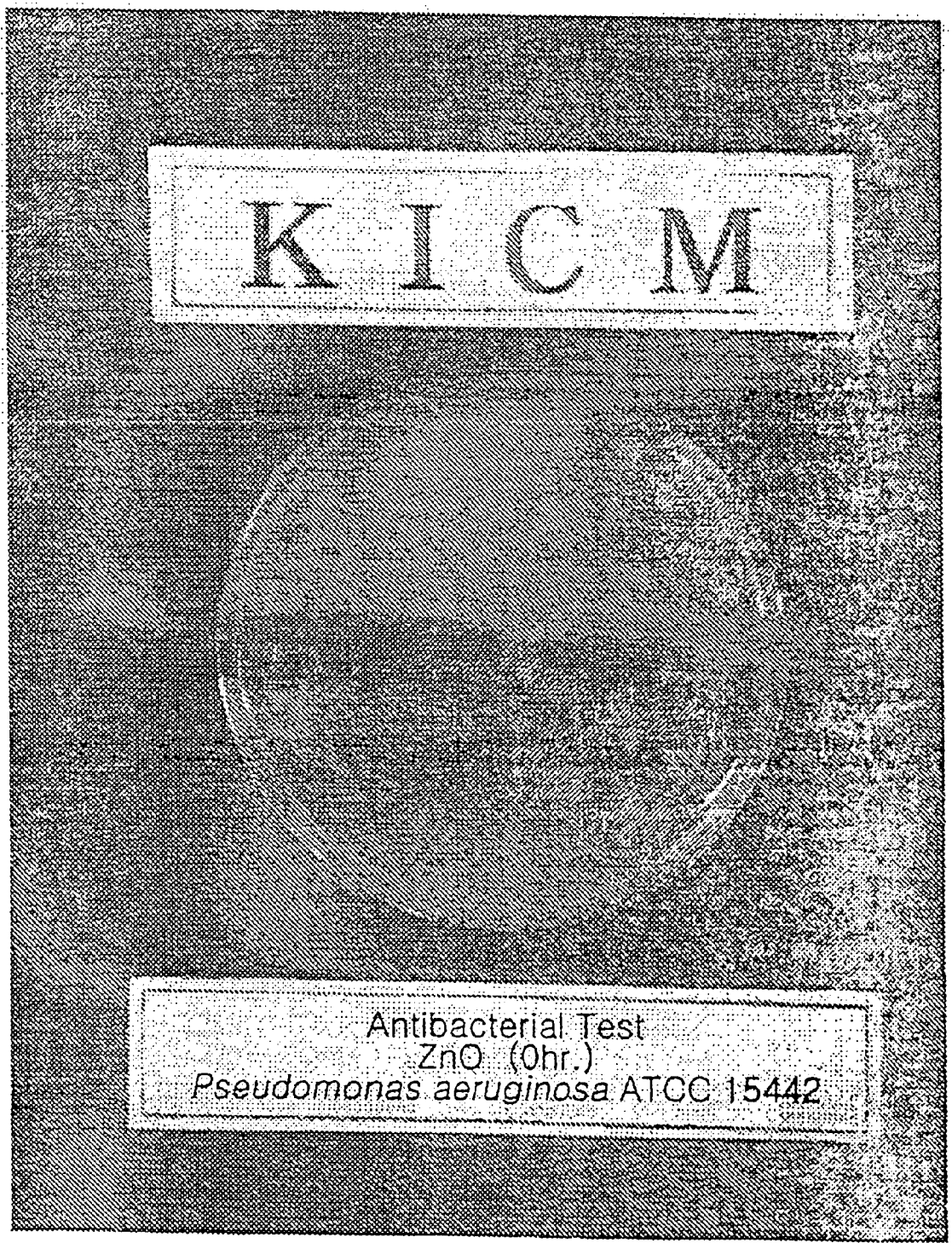
FIG. 3a is a photograph showing a standard sample comprising ZnO combined with zinc hydroxide, and *Pseudomonas aeruginosa;*
Figure 3B:
FIG. 3b is a photograph showing the growth of *Pseudomonas aeruginosa* after culturing the standard sample of FIG. 3a for 24 hours.

Also, far-infrared emission efficiencies of the alkaline oxides and hydroxides were obtained and are shown in Table 1. To this end, a measurement was made of the far-infrared emission power of each of the oxides and hydroxides shown in Table 1 with the aid of a far-infrared analyzer, which was then used to measure the far-infrared emission power of an ideal black body at 50° C. according to wavelengths. The far-infrared emissivity was defined as an area ratio of the emission power of the sample to the emission power of the ideal black body. Emission spectra of zinc oxide and magnesium oxide are given, along with that of an ideal black body, in FIGS. 1a and 1b, respectively.

The MgO and ZnO powders were tested for antibacterial activity by the shake flask method according to KICM-FIR-1002 in Korea Institute of Construction Materials.

*E. coli* (ATCC 25922) and *Pseudomonas aeruginosa* (ATCC 15422) were admixed with the emission powders containing MgO and ZnO to give standard samples which were then cultured in broths. The inhibition rate of an emission powder against bacteria was expressed by the viable cell counts as a percentage of the total viable cell count of the standard sample. The results are given in Table 1, below. Also, the test bacteria in the standard samples prior to culture and after 24 hr culture are shown in FIGS. 2a to 3b.

TABLE 1

| Material No. | Powder | pH of Saturate Aqueous Sol'n | Far IR Emissivity | *E. coli* Death Rate(%) | *P. aeruginosa* Death Rate(%) |
|---|---|---|---|---|---|
| 1 | ZnO | 7.65 | 0.930 | 99.7 | 99.7 |
| 2 | MgO | 10.25 | 0.933 | 99.7 | 99.7 |
| 3 | Zn(OH)$_2$ | 7.75 | 0.935 | 99.7 | 100 |
| 4 | Mg(OH)$_2$ | 10.45 | 0.941 | 100 | 100 |
| C. 1 | TiO$_2$ | 6.7 | 0.923 | 81.5 | 0 |
| C. 2 | Al$_2$O$_3$ | 6.7 | 0.923 | 0 | 0 |
| C. 3 | SiO$_2$ | 6.7 | 0.918 | 10.5 | 0 |
| C. 4 | CaO | 12.35 | 0.915 | 100 | 100 |
| C. 5 | Na$_2$O | >14 | 0.908 | 100 | 100 |
| C. 6 | Ca(OH)$_2$ | 12.57 | 0.918 | 100 | 100 |
| C. 7 | NaOH | >14 | 0.909 | 100 | 100 |

As seen in Table 1, white Al$_2$O$_3$, TiO$_2$ and SiO$_2$ powders had no influence on the pH of the distilled water even when they were dissolved. The solution of the alkaline oxides ZnO, MgO, CaO and Na$_2$O in water showed alkaline pH values as they were partially dissolved from their surface to form the hydroxides Zn(OH)$_2$, Mg(OH)$_2$, Ca(OH)$_2$ and NaOH, respectively. Also, Zn(OH)$_2$, Mg(OH)$_2$, Ca(OH)$_2$ and NaOH powders themselves were dissolved in the same amounts as their corresponding oxides in water, followed by measuring pH values of the resulting aqueous solutions. As apparent from the data of Table 1, the aqueous solutions of the oxides have almost the same pH values as those of their corresponding hydroxide powders. This is because, upon contact with moisture, as mentioned above, the alkaline oxides ZnO, MgO, CaO and Na$_2$O allow their surfaces to be formed to hydroxides which act to increase the pH values of the solutions.

With strong alkalinity, CaO, Na$_2$O, Ca(OH)$_2$ and NaOH are disadvantageous in practical application because they may cause an adverse effect on the body. In contrast, ZnO, MgO, Zn(OH)$_2$ and Mg(OH)$_2$ allowed for the alkalinity which is weak enough not to adversely affect the body, but potent enough to control the growth of bacteria.

EXAMPLE 2

After being placed in an autoclave, MgO was subjected to hydration at 110° C. for different time periods to give samples with different $Mg(OH)_2$ contents. The Mg(OH)2 contents in the powders were measured by thermo gravimetric analysis. The hydration content was expressed by the weight change as a percentage of the theoretical weight change ($Mg(OH)_2$=MgO+$H_2O$, 30.8% by weight) upon thermo gravimetric analysis.

TABLE 2

MgO Particle sizes and $Mg(OH)_2$ Content Change with Hydration Time

| Material No. | Initial Particle Size of MgO | Hydration time | | |
|---|---|---|---|---|
| | | 1 hr (wt %) | 2 hr (wt %) | 6 hr (wt %) |
| C. 8 | <100 meshes | 10 | 14 | 25 |
| 5 | 100~200 meshes | 17 | 28 | 43 |
| 6 | 200~325 meshes | 31 | 47 | 54 |
| 7 | >325 meshes | 60 | 77 | 88 |

As seen in Table 2, the hydration of MgO to $Mg(OH)_2$ increases with hydration time. Also, it is found that the content of $Mg(OH)_2$ formed is dependent on initial MgO particle sizes. Therefore, pulverization of MgO to more fine particles guarantees samples with larger $Mg(OH)_2$ contents.

At a MgO particle size of approximately 100 meshes or larger, the $Mg(OH)_2$ amount generated, even if the time period is extended, was not so large as to show sufficient antibacterial activity and far-infrared emission. Thus, it is preferred that MgO is pulverized to a particle size 100 meshes or less than.

EXAMPLE 3

Each of the samples of Example 2, which contained the $Mg(OH)_2$ resulting from the hydration of MgO, was measured for particle size and the results are given in Table 3, below. The measurement of the particle size resorted to a specific surface area analyzer (Manufactured by Micromeritics Inc.).

TABLE 3

| Material No. | Initial particle size | Specific Surface Area with Hydration Time (m²/g) | | | |
|---|---|---|---|---|---|
| | | 0 hr | 1 hr | 2 hr | 6 hr |
| C. 8 | <100 meshes | 0.3 | 0.68 | 0.79 | 0.76 |
| 5 | 100~200 meshes | 0.53 | 1.03 | 1.21 | 1.22 |
| 6 | 200~325 meshes | 0.67 | 1.68 | 2.45 | 2.38 |
| 7 | >325 meshes | 0.98 | 3.72 | 4.11 | 3.99 |

It is apparent from the data of Table 3 that the powder was increased in specific surface area with the extension of the hydration of MgO. This is because fine $Mg(OH)_2$ was generated by hydration. However, the specific surface area was not found to increase any more after 6 hour hydration because the $Mg(OH)_2$ already formed grew during the long hydration time period.

Meanwhile, MgO powder with an initial size of 100 meshes did not provide a hydration content of more than 30%, nor exhibit even a specific surface area of 1.0 m²/g though the hydration was carried out for as long as 6 hours.

EXAMPLE 4

Each of the sample containing $Mg(OH)_2$ was evaluated for far-infrared emissivity with the aid of a Fourier transform infrared spectrometer (Manufactured by-Midac Corporation). Far-infrared emissivity of the samples, along with their preparation conditions and $Mg(OH)_2$ contents, are summarized in Table 4, below.

The far-infrared emissivity of a sample was expressed as a ratio between the area under the emission curve plotted by the emission power versus wavelengths for the sample and the area under the emission curve obtained from an ideal black body at 50° C. In this regard, the area under the curve plotted for an sample by the emission powers versus wavelengths over the far-infrared emission band (2.5 to 20 µm) is defined as the far-infrared energy of the sample.

TABLE 4

| Material No. | Initial particle size (mesh) | Rxn Time (hr) | $Mg(OH)_2$ (wt %) | Specific Surface Area (m²/g) | Far IR Emissivity |
|---|---|---|---|---|---|
| C. 9 | <100 | 6 | 25 | 0.76 | 0.925 |
| 8 | 100~200 | 1 | 17 | 1.03 | 0.923 |
| 9 | 100~200 | 2 | 28 | 1.21 | 0.928 |
| 10 | 200~325 | 1 | 31 | 1.68 | 0.929 |
| 11 | 100~200 | 6 | 43 | 1.22 | 0.933 |
| 12 | 200~325 | 2 | 47 | 2.45 | 0.935 |
| 13 | 200~325 | 6 | 54 | 2.38 | 0.938 |
| 14 | >325 | 1 | 60 | 3.72 | 0.941 |
| 15 | >325 | 2 | 77 | 4.11 | 0.944 |
| 16 | >325 | 6 | 88 | 3.99 | 0.947 |
| C. 10 | >325 | 0 | 60 | 0.98 | 0.916 |

As seen in Sample Nos. 8 to 16, the far-infrared emissivity increased almost linearly with the increase of $Mg(OH)_2$ content. An increase in $Mg(OH)_2$ content resulted in an increase in the number of fine particles and thus in specific surface area. This indicates that a powder containing $Mg(OH)_2$ can be applied to far-infrared radiation paint. In contrast, superior as it is in terms of far-infrared emissivity, Comparative Sample No. C. 9 is unsuitable for use in paint because of its small specific surface area.

EXAMPLE 5

Commercially available, reagent grade MgO powder with a purity of 99% or higher and reagent grade $Mg(OH)_2$ powder which was made from seawater were evaluated for far-infrared emissivity. The MgO in commercially current use was found to have a far-infrared emissivity of 0.904 as measured by a Fourier transform infrared spectrometer. On the other hand, the far-infrared emissivity of the $Mg(OH)_2$ made from seawater was measured to be 0.946 which is still higher than the value of the commercially available MgO. From these results, it can be understood that a far-infrared emission powder containing $Mg(OH)_2$ may be not limited to the $Mg(OH)_2$ hydrated from MgO, but may be prepared from the $Mg(OH)_2$ extracted from seawater.

EXAMPLE 6

Far-infrared emission powders were combined with a polyester resin as shown in Table 5, below, to prepare coating materials. Thereafter, they were coated at different dry thicknesses on electromagnetic shield steel plates, each having a maximum permeability of 3,000 under time-varying magnetic fields at low frequencies with a carbon content of 0.003%, by use of a bar coater. The dry thicknesses formed are also given in Table 5, below. After the application of the coating materials, coatings on the steel plates were thermally cured at 225° C. to produce polyester-coated steel plates.

The polyester-coated steel plates were evaluated for far-infrared emissivity over the wavelength band of 5 to 20 µm and the results are given in Table 5, below.

To test the steel plates for antibacterial activity, a compression method according to KICM-FIR-1002 was used. *E. coli* (ATCC 25922) and *Pseudomonas aeruginosa* (ATCC 15442) were inoculated in standard samples (lacking antibacterial ceramic) and test samples containing antibacterial emission powder, which were then covered with other samples, followed by culturing the bacteria at 37° C. for 24 hours. The death rate of the bacteria was obtained by measuring the viable cells in the test sample as a percentage of the viable cells in the standard sample, and the results are given in Table 5, below.

TABLE 5

| Material No. | Emission Powder | Powder (wt parts/ PE 100 wt parts) | Coating Thick. ($\mu$m) | Far IR Emissivity | E. coli Death Rate (%) | P. aeruginosa Death Rate (%) |
|---|---|---|---|---|---|---|
| C. 11 | None | 0 | 20 | 0.834 | 0 | 0 |
| 17 | MgO | 30 | 5 | 0.867 | 99.3 | 93.4 |
| 18 | MgO | 30 | 10 | 0.895 | 99.9 | 99.3 |
| 19 | MgO | 5 | 20 | 0.868 | 98.5 | 93.6 |
| 20 | MgO | 10 | 20 | 0.890 | 98.9 | 94.9 |
| 21 | MgO | 20 | 20 | 0.923 | 99.3 | 93.7 |
| 22 | MgO | 30 | 20 | 0.924 | 99.3 | 99.3 |
| C. 12 | ZnO | 15 | 20 | 0.904 | 29.7 | 88.7 |
| 23 | ZnO | 25 | 20 | 0.910 | 99.7 | 93.6 |
| 24 | ZnO | 35 | 20 | 0.912 | 99.6 | 93.8 |
| C. 13 | $CaCO_3$ | 10 | 20 | 0.897 | 24.5 | 20.0 |
| C. 14 | $CaCO_3$ | 20 | 20 | 0.916 | 96.7 | 80.6 |
| 25 | $CaCO_3$ | 30 | 20 | 0.925 | 98.7 | 99.3 |

As apparent from Table 5, the steel plate treated with Comparative Material No. C. 11 was found to be very poor in far-infrared emissivity and have to no antibacterial activity.

The far-infrared emissivity increased with the increase of the coating thickness as seen in Material Nos. 17 and 18. However, the antibacterial activity was independent on the coating thickness. Even at a thickness of 5 to 10 $\mu$m, a death rate of higher than 90% could be obtained. Further, Material Nos. 17 and 18 showed a death rate of higher than 90% even if they were somewhat poor in far-infrared emissivity. By virtue of such properties, Material Nos. 17 and 18 can be applied for fingerprint-resistant coatings and thin film coatings as well as PCM coatings. However, the far-infrared emissivity of Material Nos. 17 and 18 also exceeds 0.85, meeting the minimal requirement for far-infrared emitters.

5–10 parts by weight of MgO per 100 parts by weight of a polyester resin is to give a death rate of higher than 90%. Steel plates coated with Material Nos. 19 and 20 had far-infrared emissivity of as low as 0.85–0.90, but potent inhibitory activity against bacteria. However, it is preferred that MgO powder is used in an amount of 10 parts by weight or more per 100 parts by weight of a resin to achieve a far-infrared emissivity of 90.0 or higher.

A death rate of 90% or higher for *E. coli* and *Pseudomonas aeruginosa* required the use of 20 parts by weight or more of ZnO (Material Nos. 23 and 24) or 30 parts by weight or more of $CaCO_3$ (Material No. 25) per 100 parts by weight of a resin.

EXAMPLE 7

Figure 4A:
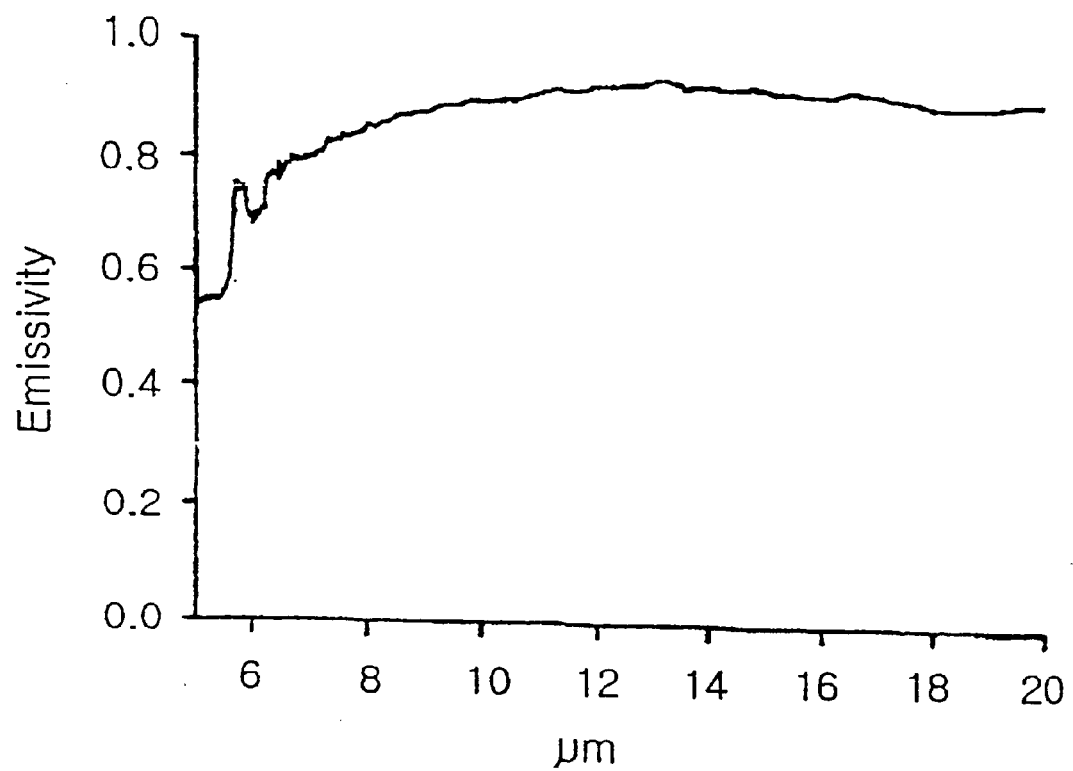
FIG. 4a is a curve in which far-infrared emissivity of a conventional polyester PCM plate is plotted versus wavelengths.
Figure 4B:
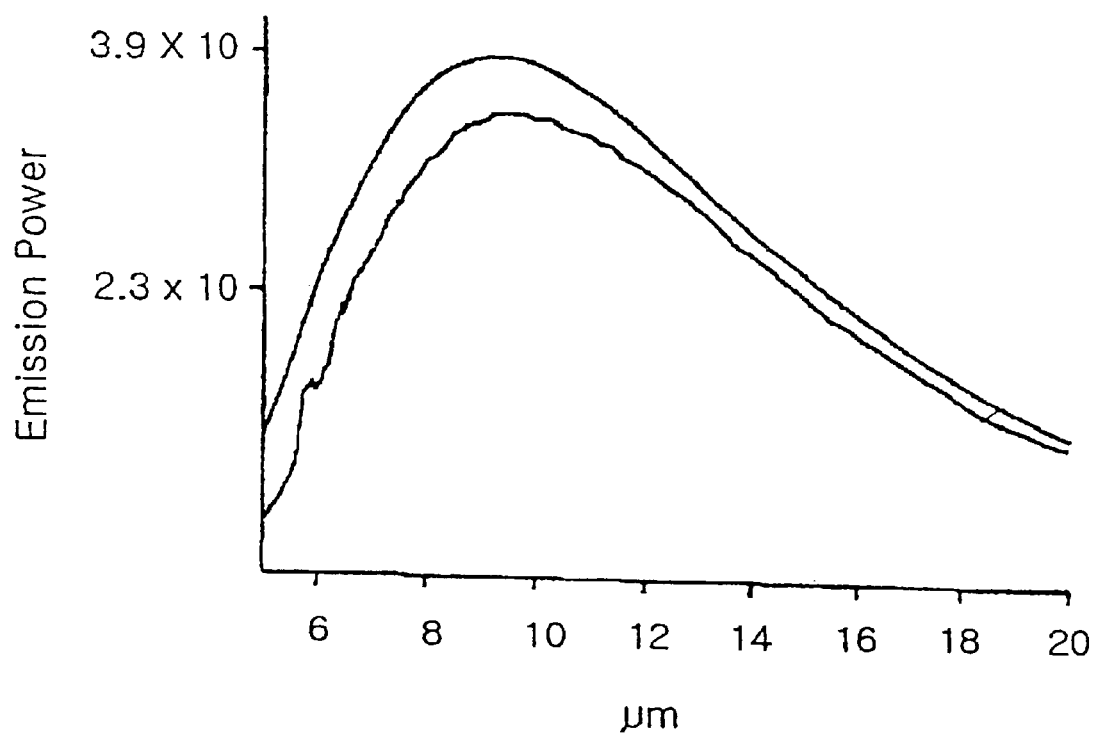
FIG. 4b shows curves in which far-infrared emission power of conventional polyester PCM plates and ideal black body are plotted versus wavelengths.

A far-infrared emission steel plate manufactured by the PCM coating method described in Korean Pat. Laid-Open Publication No. 1998-8329 exhibits a far-infrared emissivity of as low as 0.5–0.8 in the band ranging from 5 to 8 $\mu$m, as shown in FIGS. 4a and 4b. This is believed to be attributed to the fact that the polyester resin is low in far-infrared emissivity in the wavelength band of 5 to 8 $\mu$m, as shown in FIG. 5.

A measurement was made of the far-infrared emissivity of various materials over certain wavelength bands, and the results are shown in FIGS. 6a to 6d and summarized in Table 6, below.

TABLE 6

| Material No. | Emitter | Note | Far IR Emissivity/ 5~8 $\mu$m | Far IR Emissivity/ 5~20 $\mu$m |
|---|---|---|---|---|
| Conventional | PCM plate | Korean Pat. Laid-Open No. 1998-8329 | 0.5–0.8 | <0.90 |
| C. 15 | PCM resin | Polyethylene | 0.70 | 0.829 |
| C. 16 | $TiO_2$ | Powder | 0.830 | 0.923 |
| C. 17 | $Al_2O_3$ | Powder | 0.823 | 0.923 |
| C. 18 | $SiO_2$ | Powder | 0.870 | 0.918 |
| 26 | ZnO | Powder | 0.901 | 0.930 |
| 27 | MgO | Powder | 0.925 | 0.943 |
| 28 | $CaCO_3$ | Powder | 0.923 | 0.940 |
| 29 | MgO + $TiO_2$ | MgO 50 wt % $TiO_2$ 50 wt % | 0.912 | 0.928 |

As seen in Table 6, there was measured various far-infrared emissivity which differed from one far-infrared emitter to another according to wavelength bands. MgO, $CaCO_3$ and ZnO (Material Nos. 26 to 28) and a mixture comprising at least one of the oxides (Material No. 29) were found to exhibit excellent far-infrared emissivity over the wavelength band of 5 to 20 $\mu$m. Even if the wavelength band is narrowed to the range of 5 to 8 $\mu$m, they were superior in terms of far-infrared emissivity. Therefore, the emission powders MgO, $CaCO_3$ and ZnO are useful for improving the emissivity of polyester resin in the wavelength band of 5 to 8 $\mu$m.

EXAMPLE 8

Emission powders were combined in predetermined amounts with a polyester resin for PCM, to prepare coating materials. The kinds and amounts of the emission powders are given in Table 7, below.

Thereafter, the coating materials were coated at different dry thicknesses on electromagnetic shield steel plates, each having a maximum permeability of 3,000 at low frequencies with a carbon content of 0.003%, by use of a bar coater. The dry thicknesses formed are also given in Table 7, below. After the application of the coating materials, coatings on the steel plates were thermally cured at 225° C. to produce polyester-coated steel plates. The polyester-coated steel plates were evaluated for far-infrared emissivity over the wavelength bands and the results are given in Table 7, below.

TABLE 7

| Material No. | Powder in resin | Powder (wt parts/PE 100 wt parts) | Coating Thick. (μm) | Far IR Emissivity/ 5~8 μm | Far IR Emissivity/ 5~20 μm |
|---|---|---|---|---|---|
| C. 19 | None | 0 | 20 | 0.721 | 0.834 |
| C. 20 | TiO$_2$ | 30 | 20 | 0.742 | 0.890 |
| C. 21 | Al$_2$O$_3$ | 30 | 20 | 0.728 | 0.902 |
| C. 22 | MgO | 10 | 20 | 0.790 | 0.890 |
| C. 23 | CaCO$_3$ | 30 | 10 | 0.798 | 0.903 |
| C. 24 | CaCO$_3$ | 30 | 30 | 0.860 | 0.927 |
| 30 | MgO | 20 | 20 | 0.858 | 0.923 |
| 31 | MgO | 80 | 20 | 0.868 | 0.927 |
| 32 | CaCO$_3$ | 30 | 20 | 0.859 | 0.925 |
| 33 | ZnO | 25 | 25 | 0.857 | 0.912 |
| 34 | MgO + TiO$_2$ | MgO 25 TiO$_2$ 25 | 25 | 0.854 | 0.916 |

As seen in Comparative Material No. C. 19, a steel plate coated with a polyester resin lacking any far-infrared emission powder had low far-infrared emissivity in the wavelength band of 5 to 8 μm owing to the low far-infrared emission properties of the polyester resin itself. In the case that Al$_2$O$_3$ or TiO$_2$ powder was contained in the polyester resin (Comparative Material Nos. C. 20 and C. 21), the far-infrared emissivity was measured to be high, on average, over the wavelength band ranging from 5 to 20 μm, but to be very poor when the wavelength band was limited to the range of 5 to 8 μm.

By contrast, when containing MgO, CaCO$_3$ and ZnO, the steel plates were, even if coated with polyester resin, measured to show far-infrared emissivity of 0.85 or higher because the far-infrared emission powders are so excellent in terms of far-infrared emissivity in the wavelength band of 5 to 8 μm as to compensate for the poor emissivity of the polyester resin, as seen in Material Nos. 30 to 34.

When the emission powder was used too little compared to the polyester resin, for example, in an amount of 10 parts by weight per 100 parts by weight of the polyester resin, as in Comparative Material No. C. 22, sufficient far-infrared emission properties could not be obtained. On the other hand, too much of the emission powder, for example, 100 parts by weight of the emission powder per 100 parts by weight may bring about a problem in compatibility with other additives, as well as deteriorating the coatability.

Figure 7:
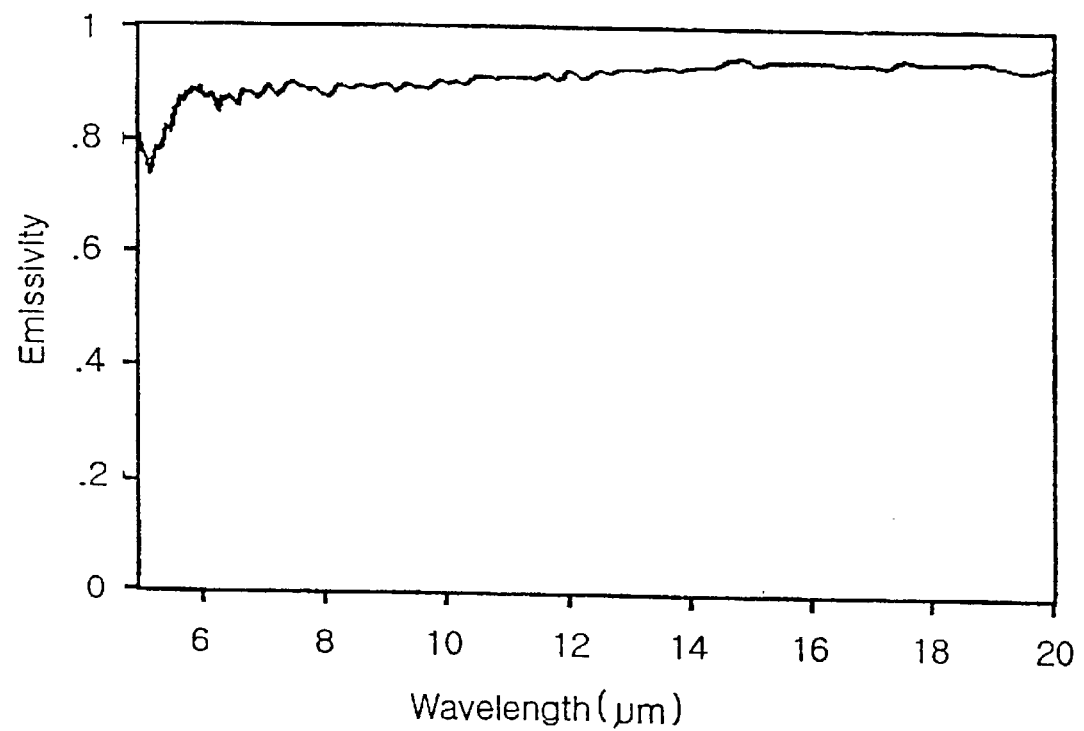
FIG. 7 is a curve in which far-infrared emissivity of a bio-wave steel plate coated with a polyester resin containing MnO and $TiO_2$ powders is plotted versus wavelengths.

Also in the steel plate coated with a polyester resin containing a mixture of MgO and TiO$_2$, like Material No. 34, an excellent far-infrared emissivity over the wavelength band of 5 to 8 μm was detected as shown in FIG. 7.

EXAMPLE 9

Steel plates coated under the conditions shown in Table 7 of Example 8 and cold-rolled steel plates having a maximum permeability of 3,000 under time-varying magnetic fields with a carbon content of 0.003% by weight were measured for electromagnetic shield efficiency and shield effect at 60 Hz.

All being made of the same material, the cold-rolled steel plates and the resin-coated steel plates showed electromagnetic shield efficiencies, which were distributed within the range of 94.5 to 95.5%. In consideration of test errors, the values are almost identical. Their electromagnetic shield effects could be also found within a narrow range from 99 to 99.2%.

Even if being applied with polyester resins containing such far-infrared emission powders, the steel plates did not show a change in their intrinsic electric and magnetic shield properties. In consequence, the far-infrared emission powders of the present invention can be applied to electromagnetic shield steel plates to allow the production of bio-wave steel plates.

EXAMPLE 10

In order to select materials suitable for use in bio-wave steel plates, known as human-friendly electromagnetic shield steel plates, various steel and non-steel materials were measured for magnetic shield efficiency at low frequencies. In this regard, magnetic shield efficiency was calculated as follows:

$$\text{Magnetic Shield Efficiency} = \frac{\text{Applied Magnetic Field} - \text{Transmitted Magnetic Field}}{\text{Applied Magnetic Field}} \times 100$$

Maximum permeability was also measured under time-varying magnetic fields at 60Hz. The results are summarized in Table 8, below.

TABLE 8

| Material No. | Plate | Composition & Property | Max. Permea. | Shield Effi. (%) |
|---|---|---|---|---|
| C. 25 | Pure Cu | Cu ≧ 99.9% | 1 | 0.4 |
| C. 26 | Pure Al | Al ≧ 99.9% | 1 | 0.3 |
| C. 27 | Cold-Rolled Steel Plate | 0.04% C- 99% ≦ Fe | 1350 | 74.8 |
| 35 | Cold-Rolled Steel Plate | 0.003% C- 99% ≦ Fe | 3700 | 96.4 |
| 36 | Cold-Rolled Steel Plate | 0.02% C- 99% ≦ Fe | 2100 | 90.4 |
| 37 | Si Steel Plate | 99% Fe—1% Si non-oriented | 4800 | 98.2 |
| 38 | Si Steel Plate | 97% Fe—3% Si oriented | 18000 | 99.0 |
| C. 28 | Stainless Steel Plate | 70% Fe—18% Ni—8% Cr— 4% other elements | 12 | 1.55 |
| C. 29 | Permalloy | 60% Ni—30% Fe—10% other elements | 25000 | 99.3 |

Pure copper and pure Al plates (Comparative Material Nos. C. 25 and C. 26), which both are superior in terms of conductivity, are too poor in maximum permeability to be suitable for use in magnetic shield at low frequencies. The stainless steel plate of Comparative Material No. C. 28 are also unsuitable for use in the present invention owing to its too low maximum permeability under time-varying magnetic fields at 60 Hz. When containing carbon in an amount greater than 0.02% by weight, a cold-rolled steel plate is drastically lowered in the maximum permeability under time-varying magnetic fields at 60 Hz, like Comparative Material No. C. 27, so that it is not suitable as a bio-wave steel plate. Permalloy such as Comparative Material No. C. 29 shows a very high permeability, but is too low in Fe content in addition to being economically unfavorable.

EXAMPLE 11

A powder containing Mg(OH)$_2$ (far-infrared emissivity 0.941), a jade powder (far-infrared emissivity 0.934), and an elvan powder (far-infrared emissivity 0.956) were processed to fine powders with a specific surface area of 1.0 m$^2$/g or higher. Then, these emission powders were mixed in a certain ratio with organic coating materials, e.g., typical paint such as those containing acrylic resins, thinner, xylene solvents, etc. The paint materials containing emission powders were applied at different thicknesses to the steel of Material No. 35 of Example 10. After being dried, the coatings thus formed with various amounts of the emission powders were evaluated for far-infrared emissivity in the thickness of coatings with the aid of a Fourier transform infrared spectrometer (Midac Corporation). The weight percentages of the far-infrared emission powders in the paint coats (after drying because of the evaporation of the thinner) (hereinafter referred to as "emitter content-in-coat") were summarized, along with the far-infrared emissivity of theirs depending on the thickness of coatings, in Table 9, below.

TABLE 9

| Material No. | Powder | Emitter in Coat (wt %) | Coating Thick. (μm) | Far IR Emissivity |
|---|---|---|---|---|
| C. 30 | None | 0 | 0 | 0.759 |
| C. 31 | None | 0 | 30 | 0.838 |
| C. 32 | Mg(OH)$_2$ | 10 | 30 | 0.877 |
| 39 | Mg(OH)$_2$ | 25 | 30 | 0.921 |
| 40 | Mg(OH)$_2$ | 33 | 30 | 0.937 |
| 41 | Mg(OH)$_2$ | 50 | 30 | 0.940 |
| C. 33 | Mg(OH)$_2$ | 67 | 30 | 0.939 |
| 42 | Mg(OH)$_2$ | 33 | 10 | 0.890 |
| 43 | Mg(OH)$_2$ | 33 | 20 | 0.930 |
| 44 | Mg(OH)$_2$ | 33 | 60 | 0.941 |
| C.34 | Mg(OH)$_2$ | 33 | 90 | 0.941 |
| 45 | Jade Powder | 33 | 30 | 0.930 |
| 46 | Elvan | 33 | 30 | 0.940 |

As apparent from the data of Table 9, a bare cold-rolled steel plate (Comparative Material No. C. 30) and a cold-rolled steel plate coated with only organic paint material lacking any far-infrared emission powder (Comparative Material No. C. 31) were of poor far-infrared emissivity. The far-infrared emission powder of the steel coated with the emission powders was found to be highly dependent upon the emitter content-in-coat. When the emitter content-in-coat is 10% by weight or lower like Comparative Material No. C. 32, the emissivity of the steel was somewhat low in emission efficiency. On the other hand, when the emitter content-in-coat was over 60% by weight as in Comparative Material No. C. 33 or the coating thickness was over 60 μm as in Comparative Material No. C. 34, the steels were not improved further in far-infrared emission efficiency with observation of deteriorated coating adhesion.

In contrast, the steel plates with emission powder-containing coatings 16–60 μm thick as in Material Nos. 39 to 46 showed excellent emission efficiency.

EXAMPLE 12

Magnetic shield test results showed that the steel plates of Material Nos. 39 to 46 of Example 11 range in magnetic shield efficiency at low frequencies from 90 to 91%, which is identical to the values of the steel plate of Material No. 36 in consideration of experimental errors. Therefore, the steel plates of the present invention can be used as bio-wave steel plates which shield harmful wavelengths and emit healthful far-infrared radiations.

The far-infrared emission powders of the present invention, as described hereinbefore, are excellent in terms of antibacterial activity and far-infrared emission properties.

Also, the far-infrared emission powders can be applied to electromagnetic shield steel plates without interruption of the intrinsic electromagnetic shield effect of the steel plates. Therefore, bio-wave steel plates which shield harmful electromagnetic waves at low frequencies, emit healthful far-infrared radiations, and are of inhibitory activity against the growth of bacteria, are provided in accordance with the present invention.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A far-infrared emission powder, which is of antibacterial activity with a pH value ranging from 7.5 to 10.5 in its saturate aqueous solution, and shows a far-infrared emissivity of 0.9 or higher.

2. The far-infrared emission powder as set forth in claim 1, wherein the far-infrared emissivity is 0.92 or higher.

3. The far-infrared emission powder as set forth in claim 1, wherein the powder has a particle size of 100 meshes or less.

4. The far-infrared emission powder as set forth in claim 1, wherein the powder has a specific surface area of 1.0 m$^2$/g or higher.

5. The far-infrared emission powder as set forth in claim 1, wherein the powder is made of a material selected from the group consisting of magnesium hydroxide, magnesium oxide, zinc hydroxide, zinc oxide, calcium carbonate, mixtures thereof, and particles containing them partially.

6. The far-infrared emission powder as set forth in claim 5, wherein the powder is made of magnesium hydroxide.

7. The far-infrared emission powder as set forth in claim 5, wherein the powder comprises in an amount of at least 17% by weight one component selected from the group consisting of magnesium hydroxide, magnesium oxide, zinc hydroxide, zinc oxide, calcium carbonate, and mixtures thereof.

8. A resin-coated steel plate with antibacterial activity and far-infrared emission properties, having a resinous coating at a dry thickness of 5 to 60 μm, said resinous coating comprising 5–100 parts by weight of a far-infrared emission powder per 100 parts by weight of a resin, said powder having a pH value ranging from 7.5 to 10.5 in its saturated aqueous solution, and showing a far-infrared emissivity of 0.9 or higher.

9. The resin-coated steel plate as set forth in claim 8, wherein the far-infrared emissivity is 0.92 or higher.

10. The resin-coated steel plate as set forth in claim 8, wherein the resinous coating is 15–30 μm thick.

11. The resin-coated steel plate as set forth in claim 8, wherein the far-infrared emission powder is made of a material selected from the group consisting of magnesium hydroxide, magnesium oxide, zinc hydroxide, zinc oxide, calcium carbonate, mixtures thereof, and particles containing them partially.

12. The resin-coated steel plate as set forth in claim 8, wherein the steel plate shows a far-infrared emissivity of 0.85 or higher and inhibits the growth of bacteria at an efficiency of 90% or higher.

13. The resin-coated steel plate as set forth in claim 12, wherein the far-infrared emissivity is 0.90 or higher.

14. The resin-coated steel plate as set forth in claim 8, wherein the far-infrared emission powder is magnesium oxide and is used in an amount of 5–100 parts by weight per 100 parts by weight of the resin and show inhibitory activity against bacteria at an inhibition efficiency of 90% or higher.

15. The resin-coated steel plate as set forth in claim 8, wherein the far-infrared emission powder is zinc oxide and is used in an amount of 20–100 parts by weight per 100 parts by weight of the resin and show inhibitory activity against bacteria at an inhibition efficiency of 90% or higher.

16. The resin-coated steel plate as set forth in claim 8, wherein the far-infrared emission powder is calcium carbonate and is used in an amount of 30–100 parts by weight per 100 parts by weight of the resin and show inhibitory activity against bacteria at an inhibition efficiency of 90% or higher.

17. The resin-coated steel plate as set forth in claim 8, wherein the resin is polyester, the far-infrared emission powder shows a far-infrared emissivity of 0.90 or higher, and the dry thickness is 15 to 30 $\mu$m.

18. The resin-coated steel plate as set forth in claim 17, wherein the steel plate shows a far-infrared emissivity of 0.90 or higher, on average, over the whole far-infrared wavelength band and a far infrared emissivity of 0.85 or higher in the far-infrared wavelength band ranging from 5 to 8 $\mu$m.

19. The resin-coated steel plate as set forth in claim 8, wherein the steel plate shows a maximum permeability of 2,000 or higher under time-varying magnetic fields at 60 Hz.

20. The resin-coated steel plate as set forth in claim 19, wherein the steel plate is a cold-rolled steel plate or comprising carbon in an amount of 0.02% by weight or less and Fe in an amount of 95% by weight or higher, or is coated with the cold-rolled steel plate.

21. The resin-coated steel plate as set forth in claim 19, wherein the steel plate is a silicon steel plate containing 0.5–3.5% by weight of Si, or is coated with the silicon steel plate.

22. The resin-coated steel plate as set forth in claim 8, wherein the coating contains the far-infrared emission powder in an amount of 25 to 50% by weight.

23. The far-infrared emission powder as set forth in claim 2, wherein the powder is made of a material selected from the group consisting of magnesium hydroxide, magnesium oxide, zinc hydroxide, zinc oxide, calcium carbonate, mixtures thereof, and particles containing them partially.

24. The far-infrared emission powder as set forth in claim 3, wherein the powder is made of a material selected from the group consisting of magnesium hydroxide, magnesium oxide, zinc hydroxide, zinc oxide, calcium carbonate, mixtures thereof, and particles containing them partially.

25. The far-infrared emission powder as set forth in claim 4, wherein the powder is made of a material selected from the group consisting of magnesium hydroxide, magnesium oxide, zinc hydroxide, zinc oxide, calcium carbonate, mixtures thereof, and particles containing them partially.

26. The resin-coated steel plate as set forth in claim 9, wherein the steel plate shows a far-infrared emissivity of 0.85 or higher and inhibits the growth of bacteria at an efficiency of 90% or higher.

27. The resin-coated steel plate as set forth in claim 10, wherein the steel plate shows a far-infrared emissivity of 0.85 or higher and inhibits the growth of bacteria at an efficiency of 90% or higher.

28. The resin-coated steel plate as set forth in claim 11, wherein the steel plate shows a far-infrared emissivity of 0.85 or higher and inhibits the growth of bacteria at an efficiency of 90% or higher.

29. The resin-coated steel plate as set forth in claim 9, wherein the far-infrared emission powder is magnesium oxide and is used in an amount of 5–100 parts by weight per 100 parts by weight of the resin and show inhibitory activity against bacteria at an inhibition efficiency of 90% or higher.

30. The resin-coated steel plate as set forth in claim 10, wherein the far-infrared emission powder is magnesium oxide and is used in an amount of 5–100 parts by weight per 100 parts by weight of the resin and show inhibitory activity against bacteria at an inhibition efficiency of 90% or higher.

31. The resin-coated steel plate as set forth in claim 11, wherein the far-infrared emission powder is magnesium oxide and is used in an amount of 5–100 parts by weight per 100 parts by weight of the resin and show inhibitory activity against bacteria at an inhibition efficiency of 90% or higher.

32. The resin-coated steel plate as set forth in claim 12, wherein the far-infrared emission powder is magnesium oxide and is used in an amount of 5–100 parts by weight per 100 parts by weight of the resin and show inhibitory activity against bacteria at an inhibition efficiency of 90% or higher.

33. The resin-coated steel plate as set forth in claim 9, wherein the far-infrared emission powder is zinc oxide and is used in an amount of 20–100 parts by weight per 100 parts by weight of the resin and show inhibitory activity against bacteria at an inhibition efficiency of 90% or higher.

34. The resin-coated steel plate as set forth in claim 10, wherein the far-infrared emission powder is zinc oxide and is used in an amount of 20–100 parts by weight per 100 parts by weight of the resin and show inhibitory activity against bacteria at an inhibition efficiency of 90% or higher.

35. The resin-coated steel plate as set forth in claim 11, wherein the far-infrared emission powder is zinc oxide and is used in an amount of 20–100 parts by weight per 100 parts by weight of the resin and show inhibitory activity against bacteria at an inhibition efficiency of 90% or higher.

36. The resin-coated steel plate as set forth in claim 12, wherein the far-infrared emission powder is zinc oxide and is used in an amount of 20–100 parts by weight per 100 parts by weight of the resin and show inhibitory activity against bacteria at an inhibition efficiency of 90% or higher.

37. The resin-coated steel plate as set forth in claim 9, wherein the far-infrared emission powder is calcium carbonate and is used in an amount of 30–100 parts by weight per 100 parts by weight of the resin and show inhibitory activity against bacteria at an inhibition efficiency of 90% or higher.

38. The resin-coated steel plate as set forth in claim 10, wherein the far-infrared emission powder is calcium carbonate and is used in an amount of 30–100 parts by weight per 100 parts by weight of the resin and show inhibitory activity against bacteria at an inhibition efficiency of 90% or higher.

39. The resin-coated steel plate as set forth in claim 11, wherein the far-infrared emission powder is calcium carbonate and is used in an amount of 30–100 parts by weight per 100 parts by weight of the resin and show inhibitory activity against bacteria at an inhibition efficiency of 90% or higher.

40. The resin-coated steel plate as set forth in claim 12, wherein the far-infrared emission powder is calcium carbonate and is used in an amount of 30–100 parts by weight per 100 parts by weight of the resin and show inhibitory activity against bacteria at an inhibition efficiency of 90% or higher.

41. The resin-coated steel plate as set forth in claim 17, wherein the steel plate shows a maximum permeability of 2,000 or higher under time-varying magnetic fields at 60 Hz.

42. The resin-coated steel plate as set forth in claim 17, wherein the coating contains the far-infrared emission powder in an amount of 25 to 50% by weight.

\* \* \* \* \*

UNITED STATES PATENT AND TRADEMARK OFFICE
CERTIFICATE OF CORRECTION

PATENT NO. : 6,773,803 B2
DATED : August 10, 2004
INVENTOR(S) : Lee et al.

It is certified that error appears in the above-identified patent and that said Letters Patent is hereby corrected as shown below:

Column 17,
Lines 2, 7 and 12, "and show inhibitory" should read -- and shows inhibitory --
Line 21, "far infrared" should read -- far-infrared --

Column 18,
Lines 1, 6, 11, 15, 18, 25, 29, 34, 39, 45, 51 and 56, "and show inhibitory" should read -- and shows inhibitory --.

Signed and Sealed this

Twenty-second Day of March, 2005

JON W. DUDAS
*Director of the United States Patent and Trademark Office*